United States Patent [19]

Haupt

[11] Patent Number: 4,685,926
[45] Date of Patent: Aug. 11, 1987

[54] ARRESTABLE KNEE JOINT

[75] Inventor: Werner Haupt, Duderstradt-Tiftlingerode, Fed. Rep. of Germany

[73] Assignee: Otto Bock Orthopaedische Industrie Besitz- und Verwaltungs-Kommanditgesellschaft, Fed. Rep. of Germany

[21] Appl. No.: 867,546

[22] Filed: May 28, 1986

[30] Foreign Application Priority Data

May 28, 1985 [DE] Fed. Rep. of Germany ....... 8515598

[51] Int. Cl.$^4$ .............................................. A61F 2/64
[52] U.S. Cl. ...................................................... 623/43
[58] Field of Search ...................................... 623/39–46

[56] References Cited

U.S. PATENT DOCUMENTS

| 3,739,404 | 6/1973 | Gelbenegger | 623/44 |
| 3,833,942 | 9/1974 | Collins | 623/43 |
| 4,232,405 | 11/1980 | Janovsky | 623/43 |
| 4,614,518 | 9/1986 | Lehneis et al. | 623/39 |

Primary Examiner—Richard J. Apley
Assistant Examiner—James Prizant
Attorney, Agent, or Firm—Schwartz, Jeffery, Schwaab, Mack, Blumenthal & Evans

[57] ABSTRACT

An arrestable knee joint, comprising a thigh member; a lower leg member; rotatably articulated on the thigh member to form a knee joint; and a mechanism for releasably arresting the members in the extended position, comprising a spring-loaded arresting element mounted in the lower leg member, structure associated with the thigh member for engaging the arresting element when the members are in the extend position, a rocker arm assembly having a first arm attached to the arresting element and a second arm extending away from a rotational axis of the rocker arm assembly on a side opposite from the first arm, and a Bowden wire inserted into the lower leg member and attached to the second arm of the rocker arm assembly. A release mechanism is provided in the thigh member.

6 Claims, 3 Drawing Figures

ARRESTABLE KNEE JOINT

BACKGROUND OF THE INVENTION

The present invention relates to a knee joint having a lower leg part rotatably articulated on a thigh part and arrested in the extended position of the knee joint. The arresting of the lower leg part can be released by means of a Bowden wire which is inserted into the lower leg part and acts on a spring-loaded locking element of the lower leg part, which locking element interacts with a locking element of the thigh part.

Arrestable knee joints serve to give the bearer of the artificial limb a safe walking feeling with the rigidly positioned knee joint and to relieve him from the risk of unintentional bending of the knee joint. It is of course necessary to provide a releasable arresting means, so that bending of the knee joint is possible for sitting or the like. The arresting means and the releasing mechanism are normally located in the thigh part of the artificial limb. In this regard, a spring-loaded pin, for example, which can be pressed out by the spring via the lower contour of the thigh part can engage into a corresponding recess of the lower leg part and provide for the arresting of the knee joint. The restoring movement is effected by pulling back the pin against the spring force. The normal attachment of the arresting mechanism in the thigh part leads to cosmetic difficulties and to problems in the operability of unlocking.

It is known to provide a projection on the thigh part, which projection grips behind a spring-loaded swivel lever of the lower leg part and therefore provides for the arresting of the knee joint. Unlocking is effected by a Bowden wire which is inserted into the lower leg part, is turned around through 180° in the hollow lower leg part and can pull the swivel lever into the contour of the lower leg part, as a result of which the arresting is released.

As a result of the pronounced inversion of the Bowden wire in a minimum of space, the unlocking force to be applied is considerably increased and there is the risk of functional disorders.

SUMMARY OF THE INVENTION

It is therefore an objection of the present invention to provide an improved knee joint. In particular, it is an object of the invention to provide a knee joint of the type mentioned at the outset in which unlocking can take place by simple means with a slight expenditure of force and without the risk of disorders caused by a Bowden wire which is bent around to a considerable degree.

In accomplishing the foregoing objects, there has been provided according to the present invention an arrestable knee joint, comprising a thigh member; a lower leg member rotatably articulated on the thigh member to form a knee joint capable of rotating between an angular orientation of the members and an extended position of the members; and means for releasably arresting the members in the extended position, comprising a spring-loaded arresting element mounted in the lower leg member, means associated with the thigh member for engaging the arresting element when the members are in the extended position, a rocker arm assembly having a first arm attached to the arresting element and a second arm extending away from a rotational axis of the rocker arm assembly on a side opposite from the first arm, and a Bowden wire inserted into the lower leg member and attached to the second arm of the rocker arm assembly.

In a preferred embodiment, the invention further comprises a release mechanism including a housing fixed to the thigh member, a circular release element rotatably mounted in the housing and a release lever on the release element, wherein the Bowden wire is fixed along a portion of the circumference of the circular release element.

Further objects, features and advantages of the present invention will become apparent from the detailed description of preferred embodiments which follows, when considered together with the attached figures of drawings.

According to the invention, the spring-loaded locking element is mounted as a spring-loaded piston in a mounting block in the lower leg part, the spring-loaded piston is held by a first arm of a rocker attached to the underside of the mounting block, and the second arm of the rocker is connected to the Bowden wire.

According to the invention, the Bowden wire can be guided virtually rectilinearly in the lower leg part. It engages on an arm of the rocker, the other arm of which is connected to the spring-loaded piston. The latter is in turn guided and retained in a mounting block. The spring-loaded piston can, for example, project out beyond the upper contour of the lower leg part and engage into a recess of the thigh part.

In a particularly preferred embodiment, the mounting block and the rocker are connected to one another by a rocker joint which is formed exclusively by a recess-web-recess or web-recess-web configuration of the sides of the mounting block and rocker, which sides lie against one another. The interlocked design of the mounting block and rocker sides which lie against one another ensures that, without additional fixing means in the assembled condition, the only movement between the mounting block and rocker possible is the rotational movement which is required for tilting. Otherwise, the rocker is held on the mounting block by the spring-loaded piston on the one hand and by the Bowden wire on the other hand.

The mounting block preferably has an extension which projects beyond the second arm of the rocker and has a guide hole for the Bowden wire. The Bowden wire is thereby guided in defined manner by the two parts, the mounting block and the rocker, which are preferably made of plastic.

The arresting mechanism can be used on both the right hand side and the left hand side if the extension of the mounting block and the second arm of the rocker extend in a fork shape and symmetrically to the center plane of the mounting block, which center plane is disposed perpendicularly on the rocker axis. In this case, the Bowden wire can be guided and retained on both sides.

If the free end of the Bowden wire rests against and is fixed to a circular-shaped release part which is provided with a release lever and is rotatably mounted in a housing fixed to the thigh part, the release part is adapted in corresponding manner to the mounting block and the rocker with respect to the right/left assembly. For this purpose, it is expedient if the housing has two inlet guides for the Bowden wire which, on the side of the release lever and on the oppositely located side, are aligned approximately tangentially to the release part. Depending on whether it is attached to the right hand or left hand side, the Bowden wire is looped around the release part in one direction or the other. The loop-around direction also enables the release lever to be either pushed downwardly or pulled upwardly, as desired, for the purpose of unlocking.

Thus the arresting mechanism, while using the same parts, can be mounted for both right-hand and left-hand actuation, as desired by the bearer of the artificial limb, and can also take into account the desire of the bearer of the artificial limb whether to effect the unlocking by the upward pull or a downward push.

BRIEF DESCRIPTION OF THE DRAWINGS

The invention is to be described in greater detail below with reference to an exemplary embodiment shown in the drawing, in which.

DETAILED DESCRIPTION OF THE PREFERRED EMBODIMENTS

Figure 1:
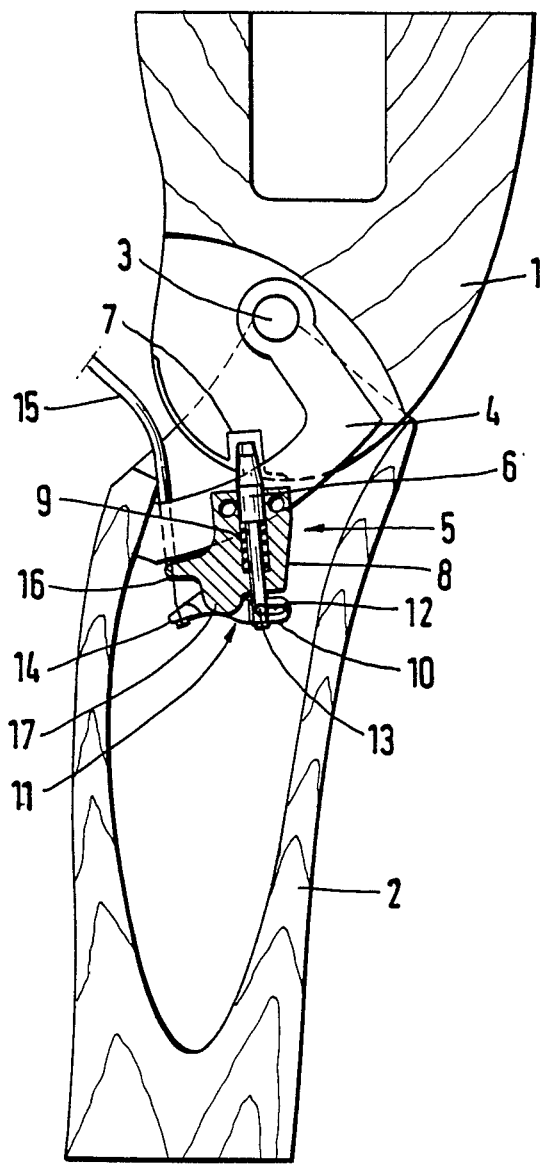
FIG. 1 is a longitudinal cross-sectional view through an arrested knee joint.

The knee joint shown in FIG. 1 consists of a thigh part 1 and a lower leg part 2 which are both made of wood in the exemplary embodiment shown. The thigh part 1 carries a rotational axis 3 on which the lower leg part 2 is articulated by means of an essentially L-shaped guide member 4 fixed to the lower leg part 2.

The lower leg part 2 carries an arresting device 5, from which an upper end of a pin 6 projects out beyond the upper contour of the lower leg part 2 and engages into a cylindrical recess 7 on the underside of the thigh part 1 when the knee joint is located in the extended position. The pin 6 is guided in a mounted block 8 and is pressed into the arresting position by a helical spring 9 held in the mounting block 8. The second end of the pin 6 projects out of the mounting block 8 and is fixed to a first arm 10 of a rocker 11. The first arm 10 of the rocker 11 encloses the end of the piston 6 and, on two oppositely located sides, has slotted holes 12 through which projects a pin 13 which penetrates through the end of the piston 6.

A second arm 14 of the rocker 11 is used for fixing a Bowden wire 15 which is inserted into the lower leg part 2. For guiding the Bowden wire 15, the mounting block has an extension 16 which projects beyond the second arm 14 of the rocker 11, is provided with a corresponding guide hole for the Bowden wire 15 and is used for supporting the Bowden wire spiral.

The extension 16 and the second arm 14 are made in a fork shape and extend symmetrically to the center plane of the mounting block 5, which center plane corresponds to the plane of the drawing and is disposed perpendicularly to the rotational axis of the rocker 11.

The rocker 11 is mounted on the mounting block 5 by means of a recess (not shown) which is defined on both sides by webs and accommodates a spherical arched-out portion 17 of the mounting block 5, which arched-out portion 17 is laterally defined by recesses for the webs of the rocker 11. This interlocked arrangement of rocker 11 and mounting block 5 forms a tilting bearing for the rocker 11, which tilting bearing does not require any further fixing means, because the rocker 11 is secured against falling away from the mounting block 5 by the Bowden wire 15 and the piston 6.

Figure 2A:
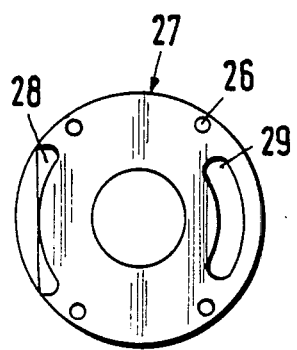
FIG. 2A is a side view of a release part with the cover cap of the housing removed.
Figure 2B:
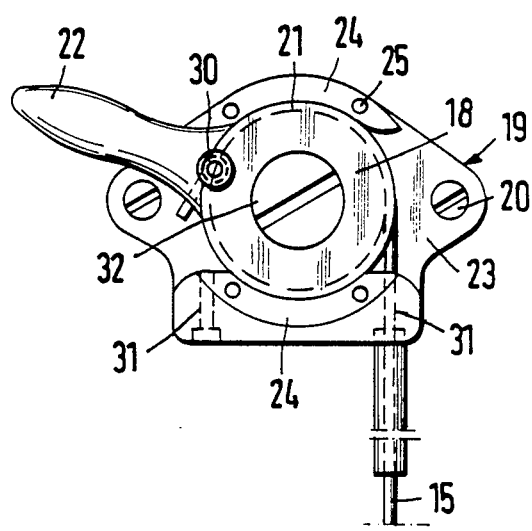
FIG. 2B is an elevation of a cover cap.

FIG. 2A shows an associated release part 18 which is mounted in a housing 19 which is firmly fixed in turn to the thigh part 1 by means of screws 20. The release part 18 is made in a circular shape and has an encircling groove 21 for guiding the Bowden wire 15. A release lever 22 is integrally molded onto the release part 18. The housing 19 has a rear support plate 23, from which rise webs 24 which border the circular release part 18 at the top and bottom and have a partially circular inner contour. The webs 24 have blind holes 25 into which can be inserted pins 26 of a housing cover 27 (shown in FIG. 2B), with which the housing can be closed. The housing cover 27 has a web section 28 which fits between the webs 24 on the side facing away from the actuating lever 22 and which assists the mounting of the release part 18. On the opposite side, there is provided in the cover part a circular-segment-shaped slotted guide 29, into which projects a fixing pin 30 for the free end of the Bowden wire 15.

It can be seen that the release part 18 can be used in the position shown in FIG. 2A, wherein the release lever 22 points toward the left, but also in a position with the release lever 22 pointing toward the right. In both cases, in order to release the arresting mechanism via the Bowden wire 15, for example, by pressing the lever 22, the Bowden wire must be guided into the other of the two inlet guides 31 in the lower web 24 of the housing 19. The two inlet guides 31 are positioned in such a way that the Bowden wire 15 guided through them is directed tangentially toward the circular release part 18 on either side of the latter. The inlet guides 31 have a step which is used for supporting this end of the Bowden wire spiral.

FIG. 2A shows the Bowden wire 15 looped around the release part 18 to an approximately semicircular extent. The Bowden wire 15 is tightened by pressing the release lever 22 downwardly, as a result of which the rocker 11 pulls the pin 6 out of the recess 7 and therefore releases the arresting mechanism.

If the Bowden wire, in the same arrangement, is guided through the other inlet guide 31 and fixed by means of the pin 30, it is apparent that lifting the release lever 22 tightens the Bowden wire 15 and therefore unlocks the knee joint. The arrangement of the two inlet guides 31 therefore enables not only the right/left mounting of the unlocking arrangement to be selected, but also enables the bearer of the artificial limb to choose to unlock the knee joint by a downward pressing or an upward pulling of the release lever 22. The release part 18 is rotatably connected to the housing 19 via a screw 32, so that pressing down or pulling up the release lever 22 takes place over a portion of a circular path.

The mounting block 8 and the rocker 11 can be made as lightweight plastic parts. The thigh part 1 and the lower leg part 2 can also be made from materials other than wood, for example, plastic.

What is claimed is:

1. An arrestable knee joint, comprising:
   a thigh member;
   a lower leg member rotatably articulated on said thigh member to form a knee joint capable of rotating between an angular orientation of said members and an extended position of said members; and
   means for releasably arresting said members in the extended position, said arresting means comprising a spring-loaded arresting element mounted in said lower leg member, means associated with said thigh member for engaging said arresting element when said members are in the extended position, a rocker arm assembly having a first arm attached to said arresting element and a second arm extending away from a rotational axis of the rocker arm assembly on a side opposite from said first arm, and a Bowden wire inserted into said lower leg member and attached to said second arm of said rocker arm assembly.

2. A knee joint as claimed in claim 1, wherein said arresting means further comprises a mounting block having an extension which projects beyond said second arm of said rocker arm assembly and which includes a guide aperture for the Bowden wire.

3. A knee joint as claimed in claim 2, wherein said extension of said mounting block and said second arm of said rocker arm assembly extend in a fork shape symmetrically to the center plane of said mounting block, said center plane being disposed perpendicularly to said rotational axis of said rocker arm assembly.

4. A knee joint as claimed in claim 1, further comprising a release mechanism including a housing fixed to said thigh member, a circular release element rotatably mounted in said housing and a release lever on said release element, wherein said Bowden wire is fixed along a portion of the circumference of said circular release element.

5. A knee joint as claimed in claim 4, wherein the housing has two inlet guides for the Bowden wire, one located on the side of the release lever and the other on the oppositely located side, said inlet guides being aligned approximately tangentially to the circular release element.

6. A knee joint as claimed in claim 2, wherein the mounting block and the rocker arm assembly are connected to one another by a rocker joint which is formed exclusively by an interfitting web and recess configuration of the sides of the mounting block and rocker arm assembly, which sides lie against one another.

* * * * *